(12) United States Patent
Liu et al.

(10) Patent No.: US 10,582,905 B2
(45) Date of Patent: Mar. 10, 2020

(54) SYSTEMS AND METHOD FOR X-RAY IMAGING

(71) Applicant: General Electric Company, Schenectady, NY (US)

(72) Inventors: James Zhengshe Liu, Salt Lake City, UT (US); Naveen Stephan Chandra, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 115 days.

(21) Appl. No.: 15/893,471

(22) Filed: Feb. 9, 2018

(65) Prior Publication Data

US 2019/0246999 A1    Aug. 15, 2019

(51) Int. Cl.
*A61B 6/00* (2006.01)
*G01B 15/02* (2006.01)

(52) U.S. Cl.
CPC ........... *A61B 6/482* (2013.01); *A61B 6/405* (2013.01); *A61B 6/42* (2013.01); *A61B 6/4441* (2013.01); *A61B 6/463* (2013.01); *A61B 6/487* (2013.01); *A61B 6/5235* (2013.01); *A61B 6/544* (2013.01); *G01B 15/02* (2013.01)

(58) Field of Classification Search
CPC ........... A61B 6/482; A61B 6/405; A61B 6/42; A61B 6/4441; A61B 6/463; A61B 6/487; A61B 6/5235; A61B 6/544; G01B 15/02
See application file for complete search history.

(56) References Cited

U.S. PATENT DOCUMENTS

| | | | |
|---|---|---|---|
| 6,438,201 B1 * | 8/2002 | Mazess | A61B 6/405 378/108 |
| 6,873,682 B2 | 3/2005 | Francke et al. | |
| 7,587,023 B2 | 9/2009 | Hur | |
| 8,430,563 B2 | 4/2013 | Uzbelger Feldman | |
| 2002/0034277 A1 * | 3/2002 | Laner | A61B 6/14 378/39 |
| 2003/0174086 A1 | 9/2003 | Francke et al. | |
| 2004/0081273 A1 * | 4/2004 | Ning | A61B 6/032 378/37 |
| 2004/0141588 A1 | 7/2004 | Francke et al. | |
| 2007/0258559 A1 | 11/2007 | Hur | |
| 2011/0150185 A1 | 6/2011 | Uzbelger Feldman | |
| 2014/0348292 A1 | 11/2014 | Yabugami | |
| 2015/0190102 A1 | 7/2015 | Bruno et al. | |
| 2018/0088061 A1 * | 3/2018 | Nakanishi | A61B 6/027 |

OTHER PUBLICATIONS

International Search Report and Written Opinion, dated May 23, 2019, PCT/US2019/017420, 11 pages.

* cited by examiner

*Primary Examiner* — Marcus H Taningco
(74) *Attorney, Agent, or Firm* — McCoy Russell LLP

(57) ABSTRACT

Methods and systems are provided for controlling an x-ray imaging system. In one embodiment, a method for an x-ray imaging system, includes acquiring, with the x-ray imaging system, a plurality of images as an x-ray tube current of the x-ray imaging system is ramping from a predefined x-ray tube current to an updated x-ray tube current, the updated x-ray tube current determined based on an estimated patient thickness estimated from a prior image acquired with the x-ray imaging system while the x-ray tube current is at the predefined x-ray tube current, combining the plurality of images into a final image, and outputting the final image for display via a display device.

20 Claims, 5 Drawing Sheets

SYSTEMS AND METHOD FOR X-RAY IMAGING

FIELD

Embodiments of the subject matter disclosed herein relate to medical imaging, and more particularly, to x-ray fluoroscopic imaging.

BACKGROUND

Non-invasive imaging technologies allow images of the internal structures or features of a patient or object to be obtained without performing an invasive procedure on the patient or object. In particular, such non-invasive imaging technologies rely on various physical principles, such as the differential transmission of x-rays through the target volume or the reflection of acoustic waves, to acquire data and to construct images or otherwise represent the observed internal features of the patient or object.

For example, in fluoroscopy and other x-ray based imaging technologies, x-ray radiation is directed toward a subject, typically a patient in a medical diagnostic application, a package or baggage in a security screening application, or a fabricated component in an industrial quality control or inspection application. A portion of the radiation impacts a detector where the image data is collected and used in an image generation process. In the images produced by such systems, it may be possible to identify and examine the internal structures and organs within a patient's body, objects within a package or container, or defects (e.g., cracks) within a fabricated component. In certain contexts, such as fluoroscopy applications used in support of interventional or navigation procedures, low-dose x-rays may be acquired at a high frame rate over an extended period to provide real-time image data that may be used to guide or navigate a tool within a patient.

During a surgical procedure assisted by fluoroscopy, surgeons often monitor progress of the surgery via a single (still) x-ray image, acquired with the fluoroscopic imaging system during a very short exposure. Due to the short exposure time, obtaining a high-quality image may be problematic and/or the patient may be subject to more radiation than desired.

BRIEF DESCRIPTION

In one embodiment, a method for an x-ray imaging system includes acquiring, with the x-ray imaging system, a plurality of images as an x-ray tube current of the x-ray imaging system is ramping from a predefined x-ray tube current to an updated x-ray tube current, the updated x-ray tube current determined based on an estimated patient thickness estimated from a prior image acquired with the x-ray imaging system while the x-ray tube current is at the predefined x-ray tube current. The method further includes combining the plurality of images into a final image and outputting the final image for display via a display device. In this way, patient thickness may be estimated during an initial phase of an imaging session, based on an image acquired during the imaging session, and used to command the x-ray imaging system to an updated x-ray current that is based on the patient thickness. As the x-ray tube current is ramping toward the updated x-ray tube current, a plurality of images is acquired and combined to generate a final image for display. By doing so, a final image of sufficient quality to view the underlying patient anatomy may be generated in a short amount of time, e.g., while the current is changing, rather than waiting until the current has reached the updated current.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
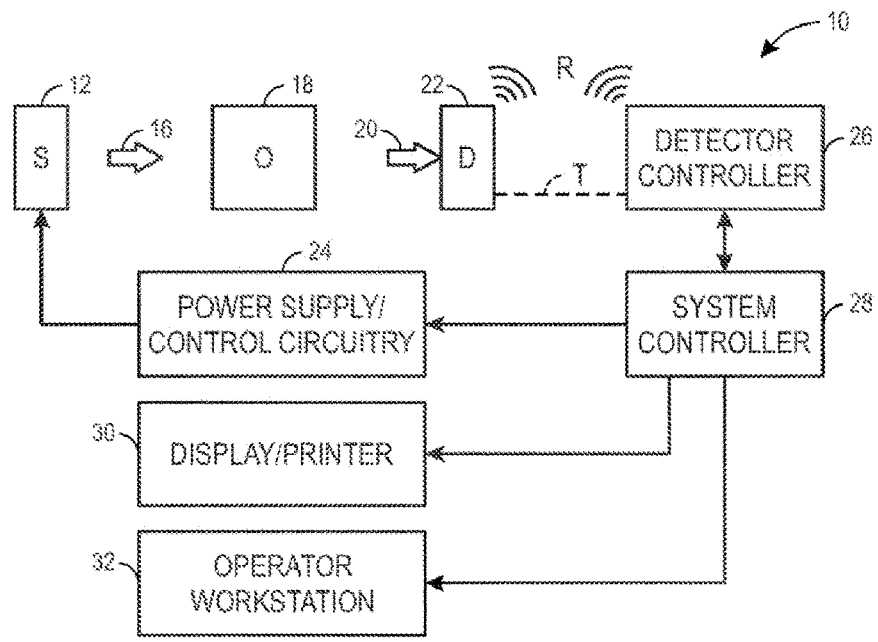
FIG. 1 depicts a block-diagram of an embodiment of a digital x-ray imaging system, in accordance with aspects of the present disclosure.

The following description relates to various embodiments of reducing exposure time during acquisition of a single skeletal x-ray image. During a surgical procedure monitored/assisted by fluoroscopic imaging, continuous, real-time x-ray images of a patient may be displayed, allowing clinicians to monitor movement of anatomical features. During such procedures, it may also be useful to occasionally monitor the patient using single, still x-ray images. To initiate fluoroscopic imaging, an exposure control pedal may be depressed, e.g., by a foot of a clinician. A quick depression and release (e.g., tap) of the exposure control pedal may indicate the clinician is requesting a single x-ray image, where prolonged depression of the exposure control pedal may indicate the clinician is requesting fluoroscopic imaging.

Typically, to obtain a high-quality x-ray image, a sequence of steps are performed before a final image is acquired and output for display. These steps may include preparing the imaging system for exposure, exposing the patient to a beam of radiation by activating a radiation source (such as an x-ray tube), and adjusting the voltage and current of the radiation source based on the brightness of the resultant images acquired by the radiation detector. Once a target brightness has been reached, further image quality adjustments may be made by applying temporal noise filters, for example. Once the images reach a target contrast to noise ratio, a final image may be acquired and output for display.

The sequence described above may be relatively lengthy, in part because the radiation source is not able to rapidly reach a commanded current with certain types of x-ray tubes. Rather, while an x-ray tube may reach a commanded voltage nearly instantaneously, the current of the x-ray tube is based on the tube voltage and a temperature of the filament of the x-ray tube. Accordingly, the x-ray tube will not reach a commanded current until the filament is heated or cooled to a certain temperature, and the time it takes to change the filament temperature may relatively long. During the time that the current is ramping toward the commanded current, images acquired may be saturated or otherwise too dark to sufficiently visualize anatomical features of the patient. Further, the actual tube voltage and current needed to acquire a high-quality image varies with patient anatomy, and thus (barring any prior information about the patient) the initial commanded voltage and current are further adjusted (e.g., based on the image brightness described above), which also lengthens the process. Thus, radiation exposure frequently continues after the clinician has released the exposure pedal, or a low-quality image is displayed.

According to embodiments disclosed herein, the sequence for obtaining a single x-ray image using a fluoroscopic imaging system (which may be referred to as a toe-tap image, due to the quick tap input by the foot of the clinician) may be shortened by commanding the fluoroscopic imaging system to transmit a beam of radiation at a predefined tube voltage and current. Then, a first (or otherwise early) image acquired by the fluoroscopic imaging system is used to estimate aspects of the anatomy being imaged, such as patient thickness and anatomy density. Based on the estimated anatomy, a new target voltage and current are determined and the system is commanded to transmit a radiation beam at the new target voltage and current. While the tube current is ramping from the predefined current to the new target current, a plurality of images are acquired. These images may then be added together to generate a final image that is output for display.

In this way, an image may be output at the time the clinician releases the exposure pedal, or at least within a small threshold after the exposure pedal is released. In doing so, the amount of radiation the patient is exposed to may be lowered, and the image may be displayed more quickly than during the lengthier sequence described above, which may be beneficial during time-sensitive procedures. Further, the image that is displayed may be of relative high-quality, and if the clinician continues to press the exposure pedal, the system may transition to fluoroscopic imaging without any delays or changes to the subsequent fluoroscopic imaging procedure.

Though a fluoroscopic imaging system is described by way of example, it should be understood that the present techniques may also be useful when applied to images acquired using other imaging modalities, such as standard, non-fluoroscopic x-ray imaging, tomosynthesis, and so forth. The present discussion of a fluoroscopic imaging modality is provided merely as an example of one suitable imaging modality.

FIG. 1 illustrates diagrammatically an imaging system 10 for acquiring and processing image data. In the illustrated embodiment, system 10 is a digital x-ray system designed both to acquire original image data and to process the image data for display. The imaging system 10 may be a stationary or mobile x-ray system. In the embodiment illustrated in FIG. 1, imaging system 10 includes a source of x-ray radiation 12 that emits a beam or stream of radiation 16 into a region in which an object or subject 18 is positioned. The x-ray radiation source 12 (which may comprise an x-ray generator and x-ray tube) is controlled by a power supply/control circuit 24 which furnishes both power and control signals for examination sequences. A portion of the radiation 20 passes through or around the subject and impacts a digital x-ray detector, represented generally at reference numeral 22. The detector 22 may be portable or permanently mounted to the system 10. In certain embodiments, the detector 22 may convert the incident x-ray photons to lower energy photons which are detected. Electrical signals are generated in response to the detected photons and these signals are processed to reconstruct an image of the features within the object or subject.

The detector array 22 may include one or more CMOS light imager panels, each separately defining an array of detector elements (e.g., pixels). Each detector element produces an electrical signal that represents the intensity of the x-ray beam incident at the position of the detector element when the beam strikes the detector 22. This signal may be digitized and sent to a monitor/display device for display. In the depicted example, the detector 22 includes or communicates with a detector controller 26 (e.g., control circuitry) which commands acquisition of the signals generated in the detector 22. In the presently illustrated embodiment, the detector 22 may communicate with the detector controller 26 via any suitable wireless communication standard (R), although the use of digital x-ray detectors 22 that communicate with the detector controller 26 through a cable (T) or some other mechanical connection are also envisaged. Alternatively, operational aspects of the detector controller 26 may be implemented on, or otherwise provided of, the detector 22 itself in some implementations. Detector controller 26 may also execute various signal processing and filtration functions, such as for initial adjustment of dynamic ranges, interleaving of digital image data, and so forth.

Both power supply/control circuit 24 and detector controller 26 are responsive to signals from a system controller 28. In general, system controller 28 commands operation of the imaging system to execute examination protocols and to process acquired image data. In the present context, system controller 28 may also include signal processing circuitry and one or more data storage structures, such as optical memory devices, magnetic memory devices, or solid-state memory devices, for storing programs and routines executed by a processor of the system 10 to carry out various functionalities, as well as for storing configuration parameters and image data. In one embodiment, a programmed computer system may be provided with hardware, circuitry, firmware, and/or software for performing the functions attributed to one or more of the power supply/control circuit 24, the detector controller 26, and/or the system controller 28.

In the embodiment illustrated in FIG. 1, system controller 28 is linked to at least one output device, such as a display or printer as indicated at reference numeral 30. The output device may include standard or special purpose monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, cloud-based network, and so forth.

The x-ray system 10 as shown in FIG. 1 may also include a variety of alternative embodiments generally configured to meet the particular needs of certain applications. For example, the x-ray system 10 may be either fixed, a mobile system, or a mobile C-arm system where the x-ray detector is either permanently mounted inside one end of the C-arm or removable from the system. Further, the x-ray system 10 may be a table and/or wall stand system in a fixed x-ray room where the x-ray detector 22 is either permanently mounted together with the system or portable. Alternatively, the x-ray system 10 may be a mobile x-ray system with a portable x-ray detector. Such a portable x-ray may be further constructed with a detachable tether or cable used to connect the detector readout electronics to the data acquisition system of the scanner. When not in use, a portable x-ray detector may be detached from the scan station for storage or transfer. In practice, the imaging system 10 may be any suitable x-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth. Further still, while an example of a flat-panel detector was described above, a digital detector system including image intensifier and video camera may be used to convert the incident x-rays to a video signal.

Figure 2:
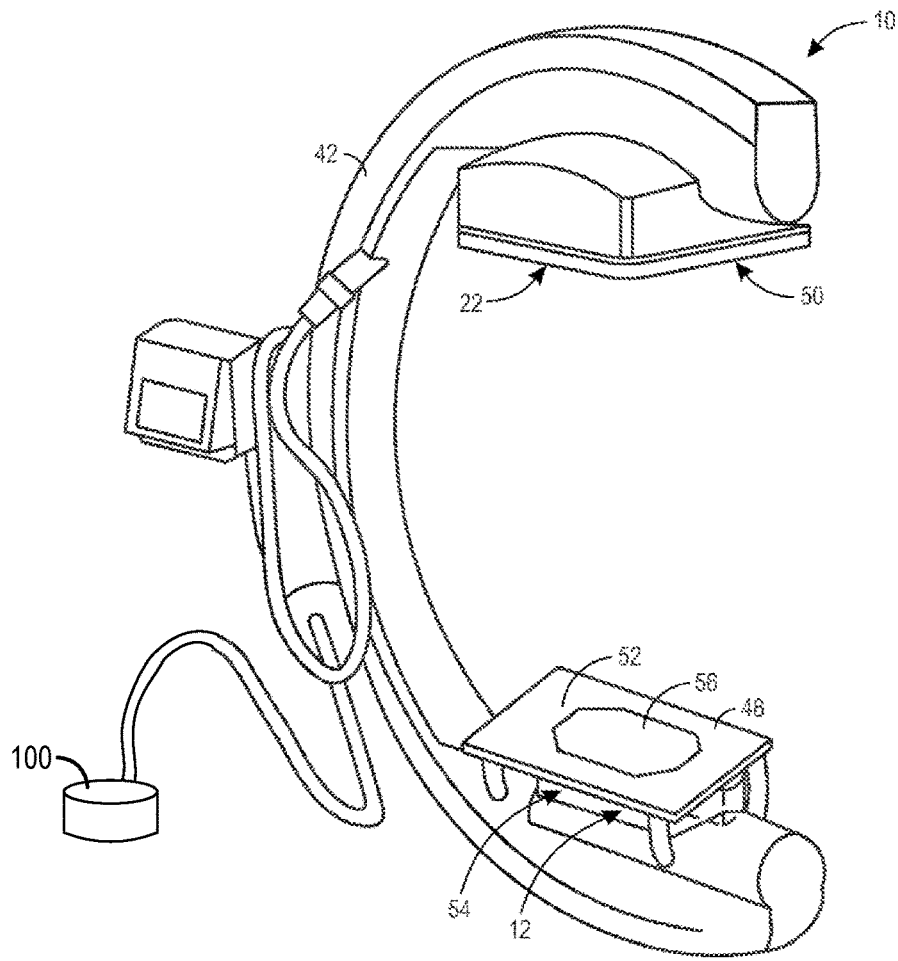
FIG. 2 depicts an implementation of an x-ray imaging system, in accordance with aspects of the present disclosure.

While the preceding schematically describes components of an x-ray based imaging system 10, including a detector and detector control and readout circuitry as discussed herein, FIG. 2 depicts an example of how such an imaging system 10 may be provided in a real-world context. As noted above, the x-ray system 10 may be implemented as a mobile x-ray device (e.g., an x-ray device comprising a C-arm, a mini C-arm, an O-arm, a non-circular arm, and so forth), and a fixed x-ray device. By way of illustration, FIG. 2 shows an x-ray imaging system 10 that comprises a C-arm x-ray device 42 configured to rotate a detector panel 22 and x-ray source 12 about a volume to be imaged. In the depicted example, the x-ray system 10 also includes a collimator 48. Any suitable x-ray source 12 can be used, including a standard x-ray source, a rotating anode x-ray source, a stationary or fixed anode x-ray source, a solid state x-ray emission source, or a fluoroscopic x-ray source 54 (as shown in FIG. 2). Any suitable x-ray detector 22 can be used, including a digital flat panel detector, an image intensifier, etc.

FIG. 2 shows an implementation in which the collimator 48 comprises an x-ray attenuating material 52 that defines an aperture 56 through which x-ray may pass, and which in turn prevents or limits x-ray emission beyond the bound of the defined aperture, thus shaping and limiting the defined beam. The collimator 48 can comprise any suitable x-ray attenuating material 52 that allows it to collimate an x-ray beam in this manner. Some examples of suitable x-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof.

Input to system controller 28 may be provided via one or more user input devices. FIG. 2 shows an example user input device in the form of a foot-pedal exposure pedal 100. Exposure pedal 100 may be connected via a suitable connection (e.g., wired or wireless) to system controller 28. Exposure pedal 100 may have a button that when depressed, signals to system controller 28 to initiate x-ray imaging. In one example, when exposure pedal 100 is depressed, a fluoroscopic imaging procedure is initiated. The fluoroscopic imaging procedure may include transmitting a beam of radiation toward a patient (e.g., via activation of x-ray source 12), where the portion of radiation that passes through or around the patient impinges on detector 22. Signals from detector 22 are then used to generate images for display. Once imaging parameters are adjusted so that the images reach a suitable level of quality (e.g., a target contrast to noise ratio), fluoroscopic imaging may commence (e.g., where the acquired images are displayed at a suitable frame rate, such as 30 fps). If the exposure pedal is released before the fluoroscopic imaging commences (e.g., during the series of steps where the imaging parameters are being adjusted to reach the target contrast to noise ratio), a toe-tap image may be displayed instead. The toe-tap image may be a single, non-moving x-ray image.

Figure 3:
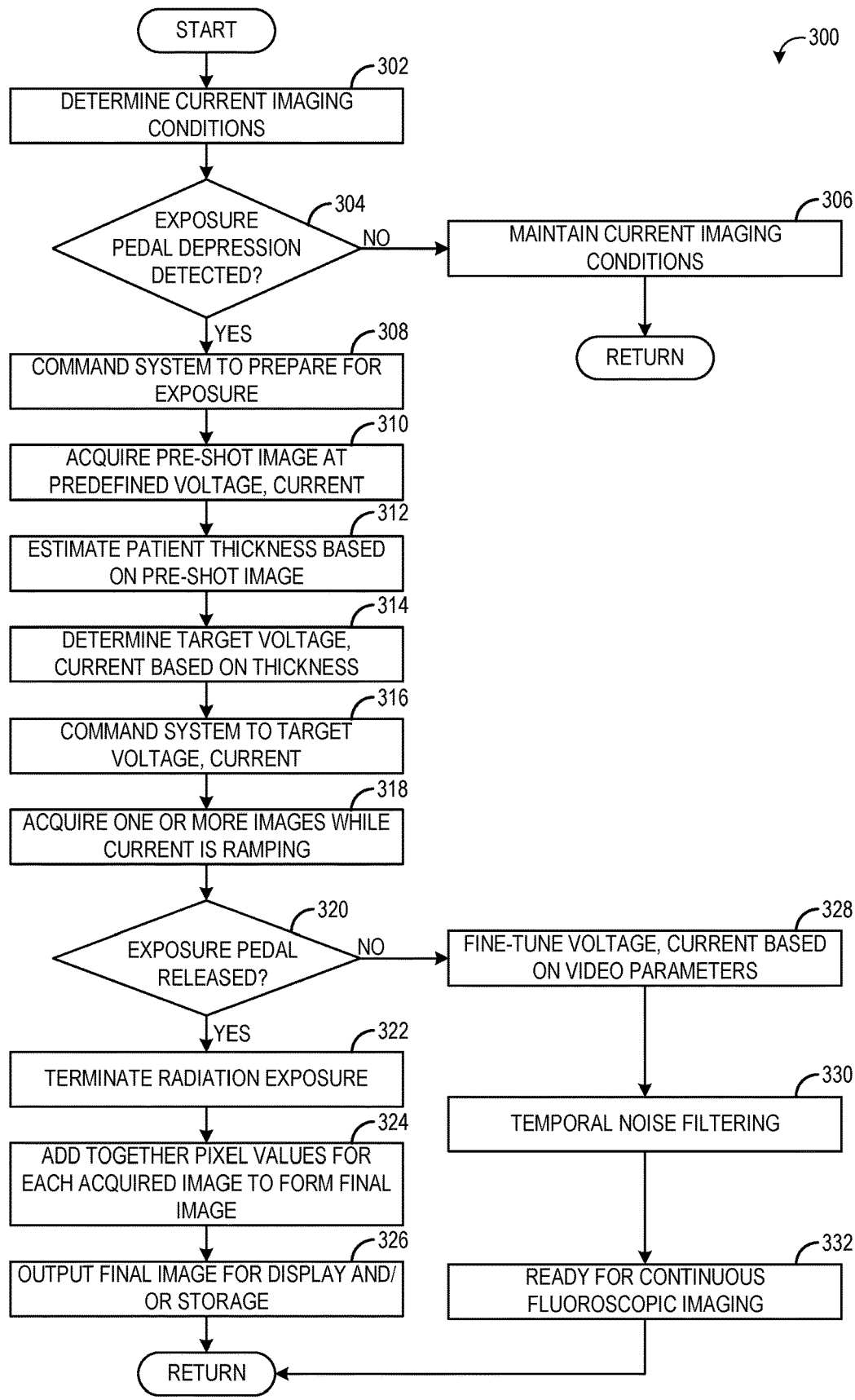
FIG. 3 is a flow chart illustrating a method for operating an x-ray imaging system.

Turning to FIG. 3, a method 300 for operating an x-ray imaging system, such as system 10 of FIGS. 1-2, is provided. The method will be described with regard to the systems and components described herein with regard to FIGS. 1-2, however it should be understood that the method may be implemented with other systems and components without departing from the scope of the present disclosure. Method 300 may be implemented as executable instructions in non-transitory memory of a computing device, such as system controller 28.

At 302, method 300 includes determining current imaging conditions. The determined current imaging conditions may include determining if x-ray imaging is currently occurring, the status of the exposure pedal (e.g., depressed or released), type of procedure being performed (such as vascular, cardiology, or spinal procedure), and/or other parameters. At 304, method 300 includes determining if an exposure pedal depression has been detected. As explained above, an x-ray imaging system, such as system 10, may include one or more user input devices, including an exposure pedal, such as exposure pedal 100. The exposure pedal may include a pedal/button that a clinician, such as a surgeon, may press to initiate x-ray imaging. To facilitate acquisition of x-ray images during surgical procedures, the exposure pedal may be a foot pedal configured to be depressed by a foot of the clinician. Thus, determining if a depression of the exposure pedal is detected may include receiving a user input signal from the exposure pedal commanding x-ray imaging to commence. The user input signal may be received continuously or periodically while the exposure pedal is depressed.

If depression of the exposure pedal is not detected, method 300 proceeds to 306 to maintain current imaging conditions. The current imaging conditions may include maintaining the radiation source of the x-ray imaging source deactivated (e.g., with no power supplied to the x-ray generator). In other examples, maintaining the current imaging parameters may include maintaining a current fluoroscopic imaging session. The detection of the depression of the exposure pedal may include detection of the exposure pedal going from released (e.g., not pressed) to being depressed. Thus, in examples where the exposure pedal is already pressed when method 300 executes, the current fluoroscopic imaging session may continue without disruption.

If depression of the exposure pedal is detected, method 300 proceeds to 308 to command the imaging system to prepare for exposure of radiation. In the exposure preparation phase, the system may command the x-ray generator and x-ray tube to prepare generating x-rays with a predetermined tube voltage (e.g., peak voltage kVp, which is the maximal voltage across the x-ray tube), a predetermined tube current (e.g., the number of electrons that jump from the cathode to the anode of the tube, represented in mA), and a predetermined pulse width. The system may also command the x-ray detector to prepare receiving x-rays with the commanded predetermined kVp, mA, and pulse width, at a predetermined frame rate, etc., and may also command the image processing unit to terminate any current tasks and prepare processing the incoming images.

For example, upon receiving a command to prepare for imaging, the x-ray detector may initiate scrubbing of the detector panel at a requested frame rate. The detector may then generate a synchronization signal when an equilibrium condition is reached and send the synchronization signal back to the system controller. The x-ray generator and x-ray tube may wait for the synchronization signal from the detector and start generating x-rays at the synchronization signal once x-ray exposure is enabled. The workstation/image processing unit may stop current activities, initialize the acquisition and image processing modules, and wait for incoming frames. Further, in some examples, during the exposure preparation phase, the filament of the x-ray tube may be pre-heated (e.g., via applying a certain amount of voltage over the filament prior to x-ray exposure) in order to reduce the amount of time for the x-ray tube to reach the commanded predefined current. For example, the filament may be heated to a predetermined temperature that is based on the predefined tube current such that the predefined tube current may be rapidly reached once exposure begins.

At 310, method 300 includes acquiring a pre-shot image at the predefined voltage and current. Once the system has commanded the components to prepare for generating/receiving x-rays, the system advances to a subsequent phase in the x-ray imaging sequence once all the components are ready (e.g., once the detector starts sending the synchronization signal, the x-ray generator sets a generator ready flag, and the workstation sets a workstation ready flag). The subsequent phase includes initiating x-ray exposure, where the x-ray tube is operated at the predefined kVp and mA. This causes x-rays to be generated and sent to, through, and around the patient, where the x-rays impinge on the detector. One or more images are generated from the signals received at the detector. Once the x-ray tube is operating at the predefined kVp and mA, a pre-shot image is acquired. The pre-shot image is then analyzed to determine patient thickness or other parameter, as described below.

The predefined kVp and mA may be selected in order to generate a pre-shot image with enough brightness to perform the estimation (described below) while delivering as low a radiation dose as possible, such as 80 kVp and 1.5 mA within a duration of 30 msec. In some examples, the predefined kVp and mA may be the same for all imaging sessions and procedure types. In other examples, the predefined kVp and mA may vary as procedure types vary. For example, different procedures are performed on different anatomy, which may result in the pre-shot images for different procedures having different expected brightness levels, and thus the predefined kVp and/or mA may be adjusted to ensure each pre-shot image has roughly the same brightness. The pre-shot image may be displayed on a display device, or it may be saved in a buffer or other temporary memory while the determination of the patient thickness (described below) is being carried out.

Figure 8:
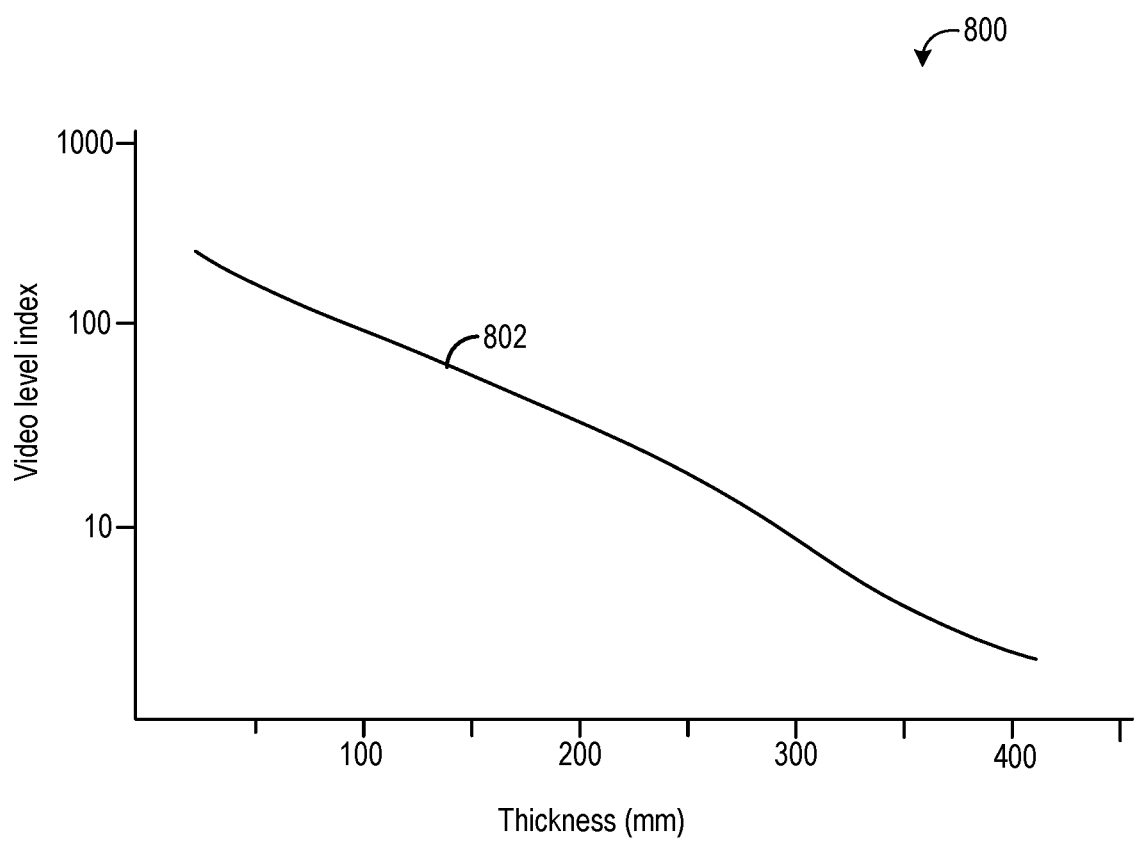
FIG. 8 shows an example curve of the calibration tables.

At 312, method 300 includes estimating patient thickness based on the pre-shot image. Patient thickness may be estimated by accessing a calibration table stored in memory of the system controller or other device, where the calibration table plots a video level index of the pre-shot image as a function of patient thickness. An example curve of the calibration tables is shown in FIG. 8. Calibration table 800 may be generated by modeling video level index of an image as functions of the thickness of polymethylmethacrylate (PMMA) and tube voltage kVp. The video level index may be an average brightness of the image in a region of interest, such as a region of the image that corresponds to a center of the detector. As illustrated in FIG. 8, the video level index may decrease logarithmically as the thickness of the PMMA increases at a given kVp.

Thus, estimating the patient thickness based on the pre-shot image may include determining the video level index of the pre-shot image and then outputting, from the calibration tables, an estimated thickness of the patient. While video level index is used herein to estimate patient thickness, other image parameters may be used instead, such as overall image brightness, saturation level, total contrast, etc. Further, in addition or alternative to estimating patient thickness, other aspects of the patient anatomy may be estimated, such as tissue density, tissue water content, tissue type, etc. Further still, while the brightness is described as being determined for a single image (e.g., frame), the video level index of the signal being generated by the detector may be evaluated.

At 314, method 300 includes determining an updated target tube voltage and updated target tube current based on the estimated thickness. In this way, based on the estimated patient thickness, updated tube voltage and updated tube current can be determined that are predicted to generate an image of reasonable quality. The updated tube voltage and current may be determined by accessing a look-up table or other data structure that indexes patient thickness to tube voltage and current. The look-up table may be stored in memory of the system controller and may be the same table for every imaging session and procedure type. In other examples, different look-up tables may be used for different procedures, different dose levels, and different pulse rates. For example, a user may select a given procedure type, such as vascular, prior to commencement of the imaging session. A look-up table specific for vascular procedures may then be selected and the updated voltage and updated current may be selected as a function of the estimated patient thickness from the vascular look-up table. In another example, if the user selects an orthopedic exam, a different look-up table specific for orthopedic exams may be selected and the updated voltage and updated current may be determined from the orthopedic table as a function of the estimated patient thickness. In an example, for the same estimated patient thickness, the vascular table may output a relatively lower voltage and higher current while the orthopedic table may output a relatively higher voltage and lower current.

At 316, method 300 includes commanding the system to operate at the updated target voltage and updated target current. For example, the updated target tube voltage and updated target tube current may be increased relative to the predefined tube voltage and the predefined tube current, e.g., if the patient thickness is relatively high. The tube voltage may be reached relatively quickly, such as within 3 msec. However, because the tube current depends on tube filament temperature in addition to tube voltage, the target tube current may take a relatively long time to be reached, such as 300 msec or more.

Thus, while the tube current is ramping toward the target current, one or more images are acquired, as indicated at 318. The images that are acquired during the ramping of the current may be saved in memory. The system may acquire as many images as possible while the current is ramping, depending on image processing constraints and the difference between the predefined tube current and the updated target tube current. For example, the x-ray system may be configured to acquire images/video signal at a rate of 30 frames/second. The ramping of the current from the predefined current to the updated target current may take 330 msec, for example. Thus, the system may acquire ten images while the current is ramping. In examples where the updated target current is equal to or within a threshold range of the predefined current (such that little or no ramping of the tube current occurs), a plurality of images are still obtained, such as six images.

At 320, method 300 determines if the exposure pedal has been released. When the exposure pedal is released, the user input signal may be terminated, indicating the operator does not desire to continue imaging. While method 300 depicts the determination of the release of the exposure pedal being performed after the one or more images have been acquired while the current is ramping, it is to be understood that the exposure pedal could be released at any time during execution of method 300. However, given the amount of time required for the clinician to depress and then release the exposure pedal, even during a quick toe-tap, it is unlikely the exposure pedal will be released before the system commands to operate at the updated target voltage and current and acquires the one or more images. In the event the exposure pedal is released before the one or more images are acquired at 318, the method may continue to execute for a short duration (e.g., 100 msec) in order to acquire the one or more images.

If the exposure pedal has been released, method 300 proceeds to 322 to terminate radiation exposure. To terminate the exposure, the power supply to the x-ray generator may be terminated, thereby causing the tube voltage and current to drop to zero and the tube to stop generating x-rays. At 324, method 300 includes adding together the pixel values for each acquired image (e.g., each image acquired at 318) to form a final image. At 326, the final image is output for display (e.g., on a display device) and/or is stored in memory.

When the one or more images are acquired at 318, tube voltage is at the updated target voltage but tube current may be changing as the tube current ramps from the predefined current toward the updated target current. Thus, each image that is acquired at 318 may be acquired at a different mA. The current does not greatly impact the contrast of these images, as contrast differences among images of the same tissue may be dictated primarily by tube voltage, which is the same for the images acquired at 318. Thus, as long as the images obtained during the toe-tap exposure have the desired tube voltage, all the images that are acquired may be used to form a final image of high quality. The most efficient way to combine the images acquired at the different tube currents is to simply add them together. However, other methods for combining the images are possible, such as a weighted average.

Returning to 320, if the exposure pedal is not released, method 300 proceeds to execute a process for continuous (or pulsed) fluoroscopic imaging. In one example, the system may transition from acquiring the one or more images while the current is ramping (without regard for the video level index) in order to generate the toe-tap image to preparing for continuous fluoroscopic imaging in response to the mAs reaching a target mAs and with the exposure pedal still being pressed, where the mAs represents the product of the actual tube current (mA) and the pulse width of each frame.

The fluoroscopic imaging process includes, at 328, fine-tuning the tube voltage and current based on video parameters, such as the video level index. The x-ray system continues to generate x-rays, the detector continues to detect the incident x-rays, and images/video signals continue to be acquired. The video level index of all subsequent acquired images may be compared to a target video level index. The target video level index may be predetermined, and may be based on the type of procedure being performed in some examples. The fine-tuning of the voltage and current compensates for any modeling errors of the patient thickness estimation.

At 330, method 300 includes temporal noise filtering the acquired images. Once the tube voltage and current have been fine-tuned so that the video level index matches the target video level index, the subsequently acquired images may be filtered to lower noise. Temporal noise filtering may include identifying regions of the acquired images that are moving (e.g., where pixel values in the region are changing from image to image) and regions of the acquired images that are not moving (e.g., where pixel values are remaining constant), and then filtering the non-moving regions. The filtering may include, for a given pixel in a non-moving region, averaging values for that pixel from a plurality of (temporally spaced) images. Once the temporal noise filtering has stabilized, the system is ready for fluoroscopic imaging, as indicated at 332. Once fluoroscopic imaging commences at 332, all acquired images may be displayed on the display device as a video feed at a suitable frame rate. Method 300 then returns.

Thus, method 300 described above provides for a quick toe-tap image acquisition process whereby an image of high quality may be obtained with a relatively short exposure time (such as 500 msec or less). The quick toe-tap image acquisition process utilizes a brightness parameter of the video signal obtained once the x-ray tube reaches a predefined tube voltage and current to estimate a thickness of the patient anatomy being imaged. The video signal used to determine the thickness may include a single frame of the video signal, referred to as the pre-shot image, and may be the first image frame acquired once the predefined tube voltage and current are reached.

The estimated patient thickness provides sufficient information about the anatomy being imaged to allow an updated target voltage and current to be determined that will generate images having acceptable quality (e.g., images at a target video level). The system is then commanded to operate at the updated target voltage and current. The updated target voltage may be reached quickly, such as within 3 msec. Thus, upon acquiring the pre-shot image and estimating the patient thickness, the tube voltage may be rapidly adjusted to the updated target voltage. The updated target voltage, because it is based on information about the anatomy being imaged, allows images of relatively high quality to be acquired in a short amount of time. Because the tube current takes a longer amount of time to reach the updated target current, the images acquired after the tube voltage is at the updated target voltage may be acquired as the tube current is changing, and before the tube current reaches the updated target current. However, the fact that the images are acquired without the tube current being at the updated target tube current may not greatly impact image quality, since the tube voltage affects image contrast (and hence the images may have acceptable levels of contrast). To compensate for the noise that may be included in the images due to the current not being at the target updated current, the acquired images may be added together, thereby reducing image noise.

While method 300 described above includes determining patient thickness based on the video level index of an image frame, other methods are possible for quickly determining patient anatomy information. For example, an operator of the x-ray system may input information about the patient to the system controller at the start of the imaging session/surgical procedure. The information may include patient weight, height, body mass index, and/or other patient information. The predefined tube voltage and predefined tube current may be selected based on the patient information (e.g., an estimation of patient thickness may be performed based on the input patient information and the predefined tube current and tube voltage may be selected based on the estimated patient thickness). Such an approach may provide for the predefined voltage and current to be tailored to the patient, increasing the likelihood high quality images can be obtained earlier in the sequence.

Figure 4:
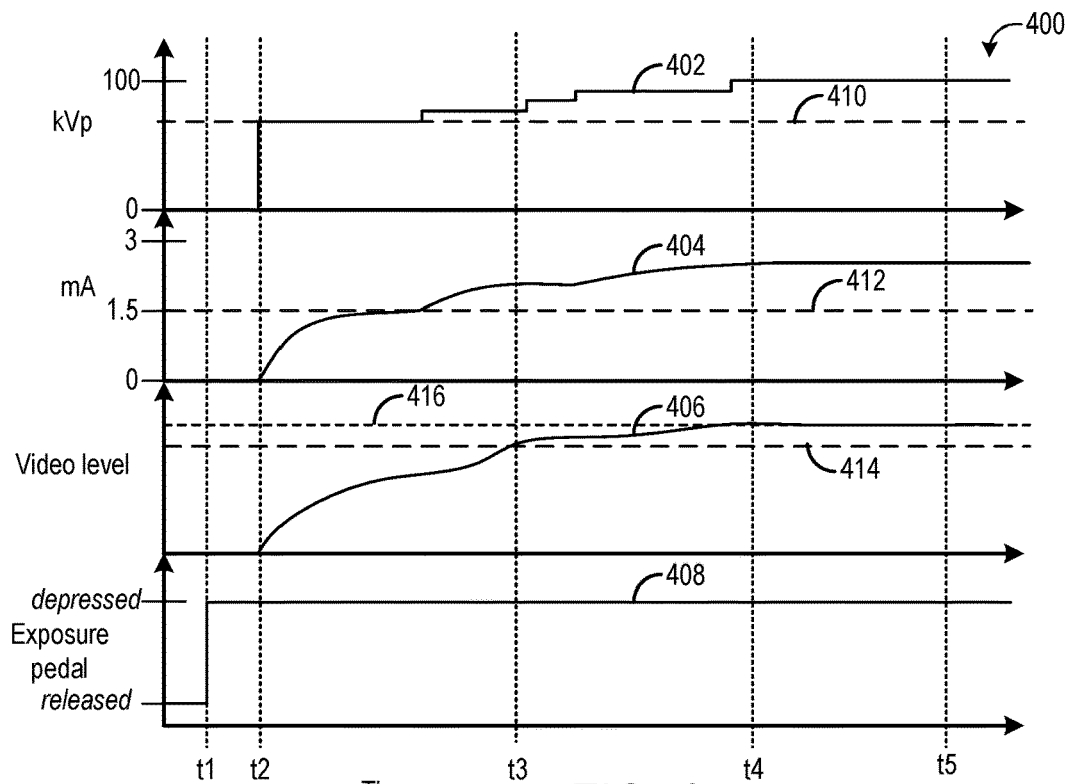
FIGS. 4-7 are timelines showing imaging parameters of interest during a plurality of fluoroscopic imaging processes.
Figure 5:
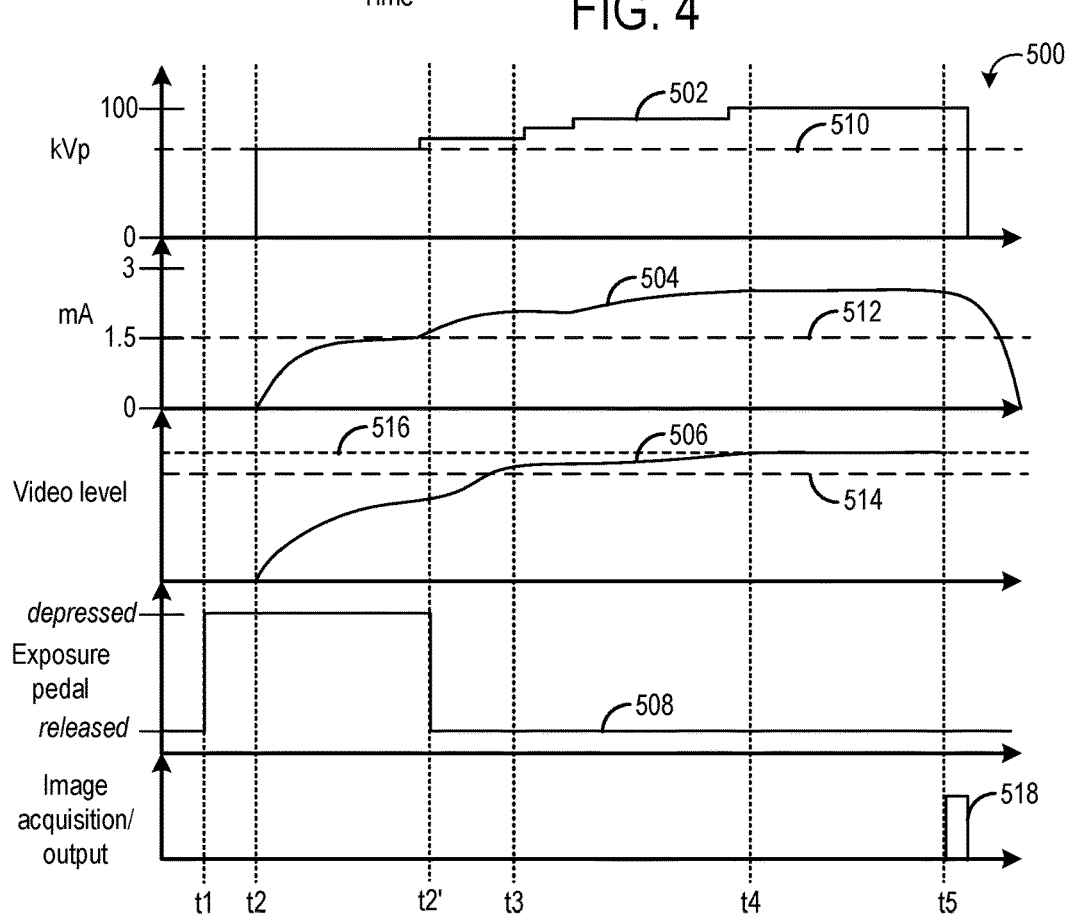
Figure 6:
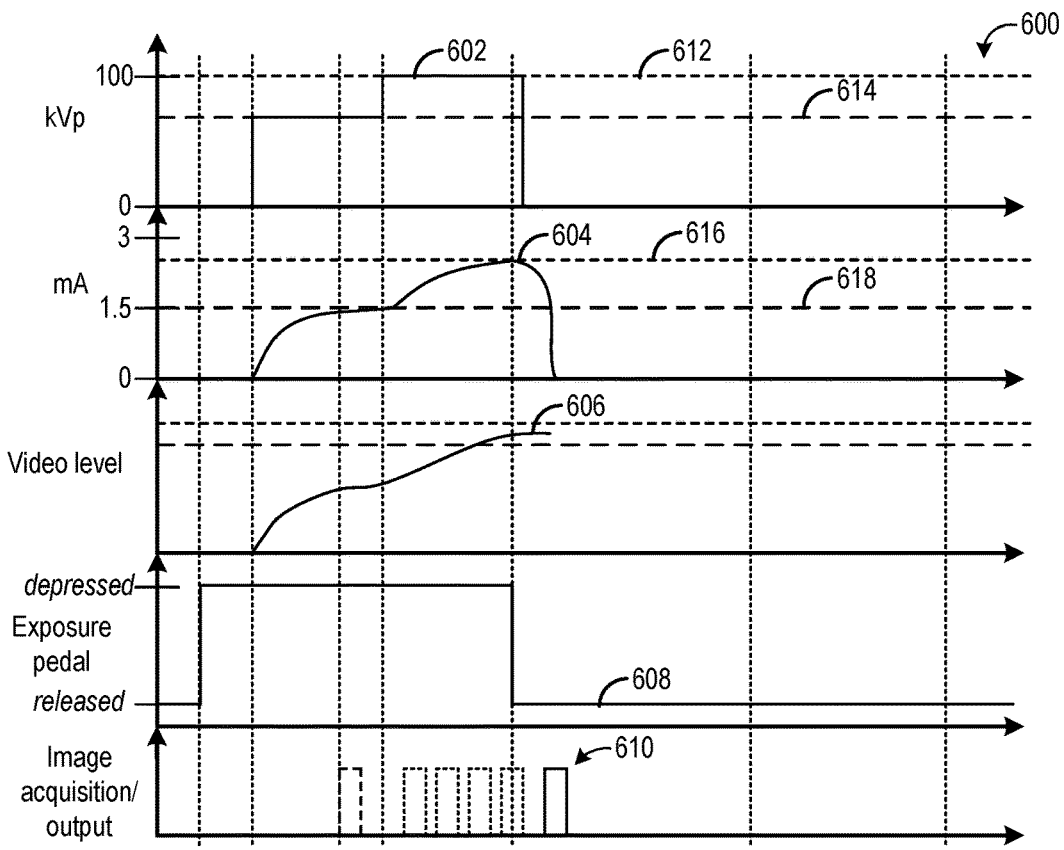
Figure 7:
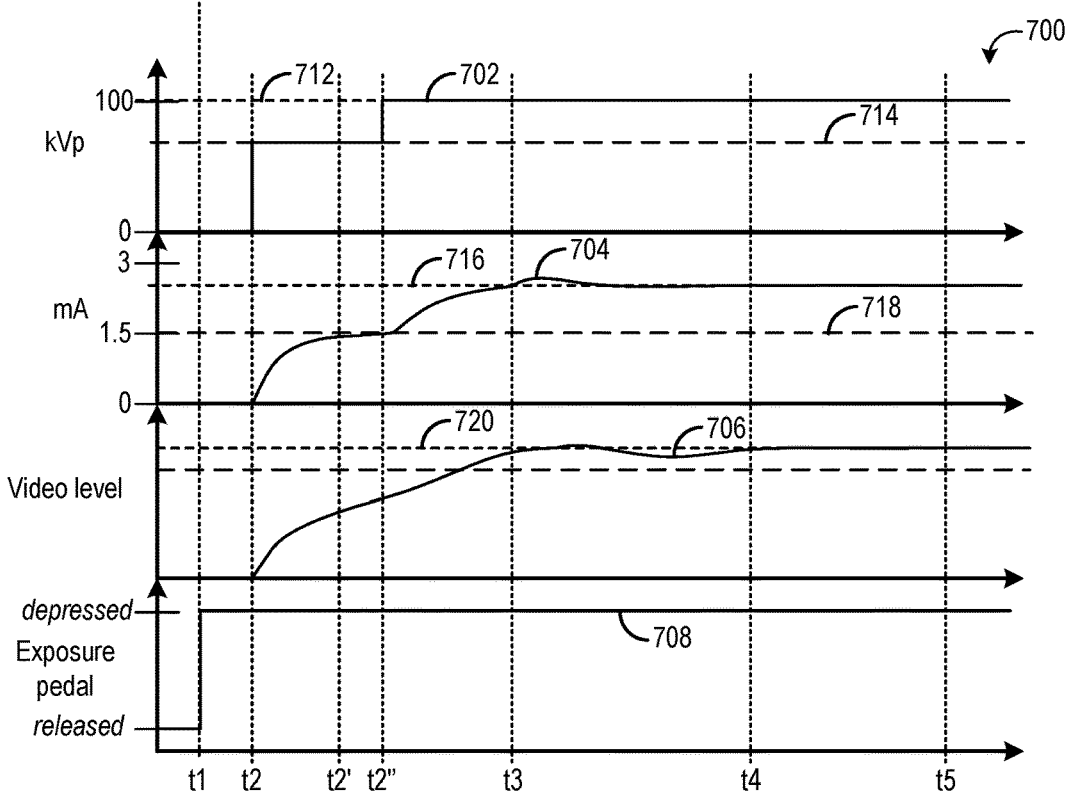

FIGS. 4-7 illustrate timelines of fluoroscopic imaging processes. FIGS. 4-5 show fluoroscopic imaging processes using a standard prior sequence where tube voltage and current are adjusted based on video level index. FIGS. 6-7 show fluoroscopic imaging processes using the expedited sequence according to the disclosure, where the tube voltage and current are adjusted based on estimated patient thickness determined from a pre-shot image. FIGS. 4-7 are all on the same time scale, such that the illustrated time points (e.g., t1, t2, t3, t4, and t5) are spaced apart by the same duration in each figure.

Referring first to FIG. 4, it shows a timeline 400 including a plurality of imaging parameters during a standard fluoroscopic imaging process. Timeline 400 includes a first plot illustrating peak tube voltage (kVp), represented by curve 402, a second plot illustrating tube current (mA), represented by curve 404, a third plot of video level index, represented by curve 406, and a fourth plot of exposure pedal status, represented by curve 408. For the plots illustrating kVp, mA, and video level index, respective values for each parameter are depicted along the y-axis, increasing from a lower value (e.g., 0) to a higher value (e.g., 100). For exposure pedal status, two states are depicted along the y-axis, a released pedal and a depressed pedal. All plots are illustrated as a function of time, and all plots are time-aligned.

Prior to time t1, the exposure pedal is released and the system is deactivated. Thus, the x-ray tube is off and voltage and current are both zero. No video signal is being generated. At time t1, an operator (e.g., surgeon) depresses the exposure pedal. The system then initiates the first phase of the imaging process, the exposure preparation phase. As described above, each imaging component is commanded to being preparing for exposure. At time t2, the components are ready for exposure and thus the second phase of the imaging process commences. In the second phase, the tube voltage and current are both commanded to predefined values in order to begin transmitting an x-ray beam to a patient. The tube voltage and current are then adjusted based on the video level index until a first target video level index is reached. Thus, power is supplied to the x-ray generator, resulting in voltage being supplied to the tube. The voltage of the x-ray tube reaches the predefined voltage, shown by line 410, at or right after t2. The predefined voltage may be based on system parameters, for example. As shown, the voltage is 80 kVp, though the illustrated voltage is exemplary and other voltages are possible. The tube current is also commanded to the predefined tube current (which as shown by line 412 is 1.5 mA), but the current ramps relatively slowly as the tube filament increases in temperature. Due to the low current, the video level index may be relatively low, though the video level index is increasing as the current increases. For example, a first target video level index is shown by line 414, referred as a "video level OK" threshold, and the video level index is below the first target video level. The current reaches the predefined current between t2 and time t3, and then continues to increase as the current is adjusted based on the video level index. Likewise, between t2 and t3, the voltage is increased based on the video level index.

At t3, the video level index reaches the first target video level index. Thus, a third phase of the process commences. In the third phase, the tube voltage and current continue to be finely-tuned based on the video level index, until the video level index reaches/stabilizes at a second target, shown by line 416. Thus, between t3 and time t4, current increases and voltage increases, as well as the video level index. However, the adjustments shown to the current and voltage are exemplary and other adjustments are possible, such as not adjusting voltage, decreasing one or both of the current and voltage, etc.

At t4, the video level index stabilizes at the second target, and thus a fourth phase of the process commences. In the fourth phase, image noise is reduced by temporally filtering the resultant images. Thus, current, voltage, and video level index are relatively constant between t4 and t5. At t5, the system is ready for fluoroscopic imaging. Thus, images are acquired and displayed on a display device at a predetermined frame rate. The exposure pedal remains pressed for the duration of the process (e.g., t1-t5) and subsequent fluoroscopic imaging.

FIG. 5 illustrates a timeline 500 including a plurality of imaging parameters during a standard toe-tap imaging process. Timeline 500 is similar to timeline 400 and includes a first plot illustrating peak tube voltage (kVp), represented by curve 502, a second plot illustrating tube current (mA), represented by curve 504, a third plot of video level index, represented by curve 506, a fourth plot of exposure pedal status, represented by curve 508, and a fifth plot of image acquisition/output, shown by curve 518. For the plots illustrating kVp, mA, and video level index, respective values for each parameter are depicted along the y-axis, increasing from a lower value (e.g., 0) to a higher value (e.g., 100). For exposure pedal status, two states are depicted along the y-axis, a released pedal and a depressed pedal. The image acquisition/output visually represents that a final image is output for display via a solid line bar. All plots are illustrated as a function of time, and all plots are time-aligned.

The toe-tap imaging process illustrated in FIG. 5 is the same as the process illustrated in FIG. 4, up to time t2' when the exposure pedal is released. Thus, between t1 and t2, the system prepares for exposure, and at time t2 exposure begins at the predefined voltage (shown by line 510) and the predefined current (shown by line 512). From time t2 to t3, current and voltage are adjusted based on the video level index, which reaches the first target (shown by line 514) before t3. At t2', the exposure pedal is released. However, due to the slowly ramping current and slow feedback loop of the video level index, the system is still operating in the second phase of the imaging process. Thus, a high quality image cannot be generated, as both the current and voltage are not at desired levels. As such, the system continues the exposure and institutes the same process as described above with respect to FIG. 4. Once the image noise has been reduced sufficiently at t5, a final image is obtained and output for display. The power to the x-ray generator is then terminated and the voltage and current both go to zero.

Thus, even when an operator performs a toe-tap on the exposure pedal, indicating that a single, still toe-tap image is desired, the system maintains exposure for a long duration after release of the exposure pedal to acquire an image of high enough quality to be displayed. The extended duration may be upward of 2 seconds, delaying display of an image during time sensitive procedures and continuing to expose the patient to radiation, even though ongoing fluoroscopic imaging is not requested.

The imaging process described herein (e.g., above with respect to FIG. 3) addresses these issues by estimating patient thickness using image information available as soon as (or quickly after) the system begins exposure, and then commanding the system to operate at updated target voltage and current. Because the voltage is reached quickly, the image contrast may be sufficiently high for generating high quality images (e.g., high contrast to noise ratio). As the current is ramping, multiple images may be acquired and then added together to generate a final image that is ready for display once the operator releases the exposure pedal. If the operator does not release the exposure pedal (and thus desires ongoing fluoroscopic imaging), the system transitions to fluoroscopic imaging.

Thus, FIGS. 6 and 7 show timelines of an example toe-tap imaging process (FIG. 6) and fluoroscopic imaging process (FIG. 7) using the expedited process described herein. Timeline 600 of FIG. 6 includes a first plot illustrating peak tube voltage (kVp), represented by curve 602, a second plot illustrating tube current (mA), represented by curve 604, a third plot of video level index, represented by curve 606, a fourth plot of exposure pedal status, represented by curve 608, and a fifth plot of image acquisition/output, shown by curve 618. For the plots illustrating kVp, mA, and video level index, respective values for each parameter are depicted along the y-axis, increasing from a lower value (e.g., 0) to a higher value (e.g., 100). For exposure pedal status, two states are depicted along the y-axis, a released pedal and a depressed pedal. The image acquisition/output visually represents that a final image is output for display via a solid line bar, with select images that may be acquired and saved, but not necessarily output for display, being shown by dashed line bars. All plots are illustrated as a function of time, and all plots are time-aligned.

Prior to time t1, the exposure pedal is released and the system is deactivated. Thus, the x-ray tube is off and voltage and current are both zero. No video signal is being generated. At time t1, an operator (e.g., surgeon) depresses the exposure pedal, which causes a user input signal to be sent to the x-ray imaging system controller. The system controller then initiates the first phase of the imaging process, the exposure preparation phase. As described above, each imaging component is commanded to being preparing for exposure, which may include preheating the filament of the x-ray tube. At time t2, the components are ready for exposure and thus the second phase of the imaging process commences. In the second phase, the tube voltage and current are both commanded to predefined values in order to begin transmitting an x-ray beam to a patient. The predefined values include a voltage of 80 kVp, shown by line 614, and a current of 1.5 mA, shown by line 618.

At time t2', the voltage and current each reach the respective predefined value. Thus, a pre-shot image is acquired at time t2', represented by the first dashed line bar of plot 610. Based on the pre-shot image, patient thickness is estimated (e.g., based on the video level index of the pre-shot image). At time t2", the voltage and current are commanded to updated target values, which were determined based on the patient thickness. The updated target voltage is 100 kVp, shown by line 612, and the updated target current is 2.5 mA, shown by line 616. The voltage reaches the updated target voltage at or right after t2". However, the current does not reach the updated target current until time t3. While the current is ramping toward the updated target current, a plurality of images are acquired, shown by the remaining four dashed line bars of plot 610. As appreciated from FIG. 6, each image that is acquired between t2" and t3 is acquired while the tube current is changing.

At t3, the operator releases the exposure pedal, thus terminating the user input signal to the system controller. The system controller finishes the acquisition of the last image and then cuts off power to the x-ray generator. As a result, after t3, voltage drops to zero and current ramps toward zero (depending on the system parameters, the current may drop similar to the voltage, e.g., nearly instantaneously). The images acquired between t2" and t3 are added together to generate a final image that is output for display, shown by the solid line bar.

As appreciated by FIG. 6, the expedited toe-tap imaging process generates a final image for display faster than the process shown in FIG. 5. For example, in FIG. 5, the final image is not output for display until t5. In contrast, the final image is output for display in FIG. 6 soon after t3, which may be approximately one second earlier than t5, at least in some examples. Thus, the patient may be exposed to less radiation during the process of FIG. 6 and the exposure may terminate when the operator releases the exposure pedal. FIG. 6 shows the video level index merely for illustrative purposes, as the video level index is not used as feedback in the control of the toe-tap process illustrated in FIG. 6.

Timeline 700 of FIG. 7 includes a first plot illustrating peak tube voltage (kVp), represented by curve 702, a second plot illustrating tube current (mA), represented by curve 704, a third plot of video level index, represented by curve 706, and a fourth plot of exposure pedal status, represented by curve 708. For the plots illustrating kVp, mA, and video level index, respective values for each parameter are depicted along the y-axis, increasing from a lower value (e.g., 0) to a higher value (e.g., 100). For exposure pedal status, two states are depicted along the y-axis, a released pedal and a depressed pedal. All plots are illustrated as a function of time, and all plots are time-aligned.

Prior to time t1, the exposure pedal is released and the system is deactivated. Thus, the x-ray tube is off and voltage and current are both zero. No video signal is being generated. At time t1, the operator depresses the exposure pedal, generating the user input signal that is sent to the system controller. The system controller then initiates the first phase of the imaging process, the exposure preparation phase. As described above, each imaging component is commanded to begin preparing for exposure, and the x-ray tube filament may be preheated. At time t2, the components are ready for exposure and thus the second phase of the imaging process commences. In the second phase, the tube voltage and current are both commanded to predefined values in order to begin transmitting an x-ray beam to a patient. The predefined values include a voltage of 80 kVp, shown by line 714, and a current of 1.5 mA, shown by line 718.

At time t2', the voltage and current each reach the respective predefined value. Thus, a pre-shot image is acquired at time t2' (not shown in FIG. 7). Based on the pre-shot image, patient thickness is estimated (e.g., based on the video level index of the pre-shot image). At time t2", the voltage and current are commanded to updated target values, which were determined based on the patient thickness. The updated target voltage is 100 kVp, shown by line 712, and the updated target current is 2.5 mA, shown by line 716. The voltage reaches the updated target voltage at or right after t2". However, the current does not reach the updated target current until time t3. While the current is ramping toward the updated target current, a plurality of images are acquired (not shown).

At time t3, the exposure pedal is still being pressed and the system controller is still receiving the user input signal. Thus, the system starts to fine-tune the current and/or voltage based on the video level index, until t4 when the second target video level index (shown by line 720) is reached and the video level index is stable. The fine-tuning of the current and/or voltage may include continuously adjusting the commanded voltage and/or current based on the video level index of subsequent obtained images. From t4 to t5, temporal noise filtering is performed. At t5, the system is ready for fluoroscopic imaging. While FIG. 7 shows the system being ready for fluoroscopic imaging at t5, similar to the process illustrated in FIG. 4, in some examples the determination/commanding of the updated target voltage and current based on patient thickness performed from t2' to t2" may allow the fluoroscopic imaging to begin faster than using the video level index as described for FIG. 4. For example, the time required for fine-tuning the current and/or voltage (from t3 to t4) may be shortened due to the current and voltage being closer to the targets needed to reach the target video level index.

A technical effect of determining patient thickness based on a brightness of a pre-shot image is the rapid determination of a target x-ray tube voltage and target x-ray tube current, lowering the amount of time needed to acquire a toe-tap image and reducing patient radiation exposure.

An example method for an x-ray imaging system includes acquiring, with the x-ray imaging system, a plurality of images as an x-ray tube current of the x-ray imaging system is ramping from a predefined x-ray tube current to an updated x-ray tube current, the updated x-ray tube current determined based on an estimated patient thickness estimated from a prior image acquired with the x-ray imaging system while the x-ray tube current is at the predefined x-ray tube current, combining the plurality of images into a final image, and outputting the final image for display via a display device. In a first example, acquiring the plurality of images as the x-ray tube current is ramping from the predefined x-ray tube current to the updated x-ray tube current comprises acquiring the plurality of images while an x-ray tube voltage is maintained at an updated x-ray tube voltage. In a second example, which optionally includes the first example, the prior image is acquired while the x-ray tube voltage is at a predefined x-ray tube voltage. In a third example, which optionally includes one or both of the first and second examples, the updated x-ray tube voltage is determined based on estimated patient thickness. In a fourth example, which optionally includes one or more or each of the first through third examples, the estimated patient thickness is estimated based on a brightness parameter of the prior image. In a fifth example, which optionally includes one or more or each of the first through fourth examples, the brightness parameter comprises a video level index of the prior image. In a sixth example, which optionally includes one or more or each of the first through fifth examples, the plurality of images are acquired responsive to receiving a user input signal commanding initiation of a fluoroscopic imaging session with the x-ray imaging system. In a seventh example, which optionally includes one or more or each of the first through sixth examples, the method further includes responsive to the user input signal being terminated at or before the final image is output for display, deactivating the x-ray tube once the final image is output for display. In an eighth example, which optionally includes one or more or each of the first through seventh examples, the method further includes, responsive to the user input signal persisting after the final image is output for display, adjusting one or more of the x-ray tube current and an x-ray tube voltage based on a video level index signal output from a radiation detector of the x-ray imaging system, and outputting subsequent acquired images for display on the display device at a predefined frame rate.

An example provides for a method for an x-ray imaging system, including estimating a thickness of an imaging subject based on a brightness of a first image acquired with the x-ray imaging system at a first x-ray tube voltage and a first x-ray tube current, commanding the x-ray imaging system to operate at a second x-ray tube voltage and a second x-ray tube current, the second x-ray tube voltage and second x-ray tube current each determined based on the estimated thickness of the imaging subject, acquiring, with the x-ray imaging system, a plurality of second images as x-ray tube current is ramping from the first x-ray tube current to the second x-ray tube current; and combining the plurality of second images into a final image and outputting the final image for display via a display device. In a first example, acquiring the plurality of second images as x-ray tube current is ramping from the first x-ray tube current to the second x-ray tube current comprises acquiring the plurality of second images as x-ray tube voltage is maintained at the second x-ray tube voltage. In a second example, which optionally includes the first example, the method further includes acquiring the first image responsive to a user input signal received by the x-ray imaging system from a user input device. In a third example, which optionally includes one or both of the first and second examples, the method further includes, responsive to the user input signal being terminated at or before the final image is output for display, deactivating the x-ray tube once the final image is output for display. In a fourth example, which optionally includes one or more or each of the first through third examples, the method further includes, responsive to the user input signal persisting after the final image is output for display, adjusting one or more of the x-ray tube current and an x-ray tube voltage based on a video level index signal output from a radiation detector of the x-ray imaging system, and outputting subsequent acquired images for display on the display device at a predefined frame rate.

An example provides for an x-ray imaging system, including a radiation source comprising an x-ray tube configured to project a beam of radiation toward a patient; a radiation detector configured to receive the beam of radiation projected by the radiation source and impinged by the patient; and a controller. The controller is configured to: responsive to receiving a user input signal requesting initiation of an imaging session, command the x-ray tube to operate at a predefined voltage and predefined current; acquire, via the radiation detector, a first image at the predefined voltage and the predefined current; estimate a thickness of the patient based on a brightness of a first image; command the x-ray tube to operate at an updated voltage and an updated current, the updated voltage and updated current each determined based on the estimated thickness of the patient; acquire, via the radiation detector, a plurality of second images as x-ray tube current is ramping from the predefined current to the target current; and combine the plurality of second images into a final image and output the final image for display via a display device. In a first example, the controller is further configured to, if the user input signal is terminated at or before the final image is output for display, deactivate the x-ray tube once the final image is output for display. In a second example, which optionally includes the first example, the controller is configured to, if the user input signal persists after outputting the final image for display, adjust one or more of the current and voltage based on a video level index signal output from the radiation detector, and output subsequent acquired images for display on the display devices at a predefined frame rate. In a third example, which optionally includes one or both of the first and second examples, the user input signal is received from an exposure pedal including a button that generates the user input signal when the button is depressed and terminates the user input signal when the button is released. In a fourth example, which optionally includes one or more or each of the first through third examples, commanding the x-ray tube to operate at the predefined voltage and the predefined current comprises preheating a filament of the x-ray tube to a target temperature, the target temperature based on the predefined current. In a fifth example, which optionally includes one or more or each of the first through fourth examples, preheating the filament comprises applying voltage to the filament.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. Are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray imaging system, comprising:
acquiring, with the x-ray imaging system, a plurality of images as an x-ray tube current of the x-ray imaging system is ramping from a predefined x-ray tube current to an updated x-ray tube current, the updated x-ray tube current determined based on an estimated patient thickness estimated from a prior image acquired with the x-ray imaging system while the x-ray tube current is at the predefined x-ray tube current;
combining the plurality of images into a final image; and
outputting the final image for display via a display device.

2. The method of claim 1, wherein acquiring the plurality of images as the x-ray tube current is ramping from the predefined x-ray tube current to the updated x-ray tube current comprises acquiring the plurality of images while an x-ray tube voltage is maintained at an updated x-ray tube voltage.

3. The method of claim 2, wherein the prior image is acquired while the x-ray tube voltage is at a predefined x-ray tube voltage.

4. The method of claim 2, wherein the updated x-ray tube voltage is determined based on the estimated patient thickness.

5. The method of claim 1, wherein the estimated patient thickness is estimated based on a brightness parameter of the prior image, and wherein the combining of the plurality of images includes adding respective pixel values of each of the plurality of images to generate the final image.

6. The method of claim 5, wherein the brightness parameter comprises a video level index of the prior image.

7. The method of claim 1, wherein the plurality of images is acquired responsive to receiving a user input signal commanding initiation of a fluoroscopic imaging session with the x-ray imaging system, and wherein each image of the plurality of images is acquired at a different x-ray tube current and a same x-ray tube voltage.

8. The method of claim 7, further comprising responsive to the user input signal being terminated at or before the final image is output for display, deactivating the x-ray tube once the final image is output for display.

9. The method of claim 8, further comprising responsive to the user input signal persisting after the final image is output for display, adjusting one or more of the x-ray tube current and an x-ray tube voltage based on a video level index signal output from a radiation detector of the x-ray imaging system, and outputting subsequent acquired images for display on the display device at a predefined frame rate.

10. A method for an x-ray imaging system, comprising:
estimating a thickness of an imaging subject based on a brightness of a first image acquired with the x-ray imaging system at a first x-ray tube voltage and a first x-ray tube current;
commanding the x-ray imaging system to operate at a second x-ray tube voltage and a second x-ray tube current, the second x-ray tube voltage and second x-ray tube current each determined based on the estimated thickness of the imaging subject;
acquiring, with the x-ray imaging system, a plurality of second images as x-ray tube current is ramping from the first x-ray tube current to the second x-ray tube current; and
combining the plurality of second images into a final image and outputting the final image for display via a display device.

11. The method of claim 10, wherein acquiring the plurality of second images as x-ray tube current is ramping from the first x-ray tube current to the second x-ray tube current comprises acquiring the plurality of second images as x-ray tube voltage is maintained at the second x-ray tube voltage.

12. The method of claim 10, further comprising acquiring the first image responsive to a user input signal received by the x-ray imaging system from a user input device.

13. The method of claim 12, further comprising responsive to the user input signal being terminated at or before the final image is output for display, deactivating the x-ray tube once the final image is output for display.

14. The method of claim 13, further comprising responsive to the user input signal persisting after the final image is output for display, adjusting one or more of the x-ray tube current and an x-ray tube voltage based on a video level index signal output from a radiation detector of the x-ray imaging system, and outputting subsequent acquired images for display on the display device at a predefined frame rate.

15. An x-ray imaging system, comprising:
a radiation source comprising an x-ray tube configured to project a beam of radiation toward a patient;
a radiation detector configured to receive the beam of radiation projected by the radiation source and impinged by the patient; and
a controller configured to:
responsive to receiving a user input signal requesting initiation of an imaging session, command the x-ray tube to operate at a predefined voltage and a predefined current;
acquire, via the radiation detector, a first image at the predefined voltage and the predefined current;
estimate a thickness of the patient based on a brightness of a first image;
command the x-ray tube to operate at an updated voltage and an updated current, the updated voltage and the updated current each determined based on the estimated thickness of the patient;
acquire, via the radiation detector, a plurality of second images as x-ray tube current is ramping from the predefined current to a target current; and
combine the plurality of second images into a final image and output the final image for display via a display device.

16. The system of claim 15, wherein the controller is further configured to, if the user input signal is terminated at or before the final image is output for display, deactivate the x-ray tube once the final image is output for display.

17. The system of claim 16, wherein the controller is configured to, if the user input signal persists after outputting the final image for display, adjust one or more of the current and voltage based on a video level index signal output from the radiation detector, and output subsequent acquired images for display on the display device at a predefined frame rate.

18. The system of claim 17, wherein the user input signal is received from an exposure pedal including a button that generates the user input signal when the button is depressed and terminates the user input signal when the button is released.

19. The system of claim 15, wherein commanding the x-ray tube to operate at the predefined voltage and the predefined current comprises preheating a filament of the x-ray tube to a target temperature, the target temperature based on the predefined current.

20. The system of claim 19, wherein preheating the filament comprises applying voltage to the filament.

\* \* \* \* \*